United States Patent [19]
Voris et al.

[11] Patent Number: 5,744,423
[45] Date of Patent: Apr. 28, 1998

[54] METHOD AND COMPOSITION FOR PROTECTING PAVEMENT STRUCTURE FROM GROWTH OF PLANTS IN SPLITS OF THE STRUCTURE

[75] Inventors: Peter Van Voris, Richland; Dominic A. Cataldo, Kennewick, both of Wash.; Frederick G. Burton, Stansbury Park, Utah; W. Eugene Skiens, Wilsonville, Oreg.

[73] Assignee: Battelle Memorial Institute, Richland, Wash.

[21] Appl. No.: 482,238

[22] Filed: Jun. 7, 1995

Related U.S. Application Data

[63] Continuation-in-part of Ser. No. 376,621, Jan. 23, 1995, abandoned, which is a continuation of Ser. No. 154,640, Nov. 18, 1993, abandoned, which is a continuation of Ser. No. 33,056, Mar. 10, 1993, abandoned, which is a continuation of Ser. No. 914,224, Jul. 13, 1992, abandoned, which is a continuation of Ser. No. 402,065, Sep. 1, 1989, abandoned, which is a continuation-in-part of Ser. No. 555,113, Nov. 23, 1983, Pat. No. 5,116,414, which is a continuation-in-part of Ser. No. 314,869, Oct. 26, 1981, abandoned, and a continuation-in-part of Ser. No. 314,810, Oct. 26, 1981, abandoned.

[51] Int. Cl.⁶ .......................... A01N 25/10; A01N 25/34; A01N 33/18
[52] U.S. Cl. ............................................. 504/116; 504/347
[58] Field of Search ........................ 504/116, 347; 71/DIG. 1

[56] References Cited

U.S. PATENT DOCUMENTS

| | | | |
|---|---|---|---|
| 3,111,403 | 11/1963 | Soper | 71/121 |
| 3,864,114 | 2/1975 | Green | 71/DIG. 1 |
| 5,116,414 | 5/1992 | Burton et al. | 71/121 |

OTHER PUBLICATIONS

Hughes, J. "Controlled Release Technology Inhibits Root Growth", Controlled Release Business & Technology, p. 15, 1989.

Battelle Technology Transfer Bulletin, Controlled–Release Chemicals for Inhibiting Plant Roots, C42–84–12–10–303, 1984.

Biobarriers in Shallow Burial Ground Stabilization, JF Cline, DA Cataldo, WE Skiens, and FG Burton, Nuclear Technology, vol. 58, Aug. 1982.

*Primary Examiner*—S. Mark Clardy
*Attorney, Agent, or Firm*—Steven Z. Szczepanski

[57] ABSTRACT

A method and device are used for controlling growth of plants in pavement splits by preventing seeds from germinating and by preventing growth of plants from existing roots in the vicinity of the splits. The growth of plants is controlled for extended periods of time (2 to 20 years). A pre-emergence herbicide and a systemic herbicide are incorporated into a polymeric matrices. The polymeric matrices are formed into shaped objects, such as, bands or cords which are then inserted into splits. The split is then filled with a sealer which permits easy migration of the herbicides therethrough. The herbicides gradually released from the shaped objects at a rate sufficient to maintain a minimal effective level of herbicide outside said sealer for a predetermined period of time.

12 Claims, 2 Drawing Sheets

METHOD AND COMPOSITION FOR PROTECTING PAVEMENT STRUCTURE FROM GROWTH OF PLANTS IN SPLITS OF THE STRUCTURE

REFERENCE TO CONTINUATION APPLICATIONS

The present application is a Continuation-in-Part of U.S. patent application Ser. No. 08/376,621, filed Jan. 23, 1995, abandoned, which is a Continuation of U.S. patent application Ser. No. 08/154,640 filed Nov. 18, 1993, now abandoned, which is a Continuation of U.S. patent application Ser. No. 08/033,056, filed Mar. 10, 1993, now abandoned, which is a continuation of U.S. patent application No. 07/914,224, filed Aug. 13, 1992, now abandoned, which is a continuation of U.S. patent application Ser. No. 07/402,065 filed Sept. 1, 1989, abandoned, which is a continuation in part of U.S. patent application Ser. No. 06/555,113 filed on Nov. 23, 1993, (now U.S. Pat. No. 5,116,414), which is a continuation-in-part of U.S. patent application Ser. Nos. 06/314,809 and 06/314,810 both filed on Oct. 26, 1981 and both now abandoned.

BACKGROUND OF THE INVENTION

The present invention relates generally to the field of controlling the growth of plants in splits found in cement or asphalt pavements. The invention, more particularly, relates to the field of long-term control of plant growth in the splits.

Pavements are usually made of asphalt and concrete but can also be constructed by a variety of building materials such as stone, brick and cobblestone. Such pavement structures including sidewalks and curbs are usually engineered with seams and/or expansion joints. The expansion joints are intended to function to either prevent or limit the formation of cracks in the pavement caused by thermal/pressure excursions such as those caused by weather.

Most commonly, cracks are caused by natural processes such as freezing and thawing of the pavement caused by weather conditions. Because of the freezing and thawing, the integrity of the joints in the pavement may be reduced or worse, cracks may form in the pavements. Further, enlargement of both the manufactured or naturally created splits can occur during severe cold weather when water infiltrates into the splits. As used in this specification and the appended claims the term "split" is defined to mean any type of divide in the pavement including cracks, joints and seams.

The problem associated with splits in the pavement can be amplified by plants. The joints, the seams and the cracks in the pavement serve as natural collection points for wind dispersed plant seeds. Moisture and soil which accumulate in the cracks provide an ideal environment for plants allowing the seeds to sprout. Upon germinating, the plants accentuate the problem of crack enlargement by further inducing the cracks. Moreover, roots of plants in the soil below pavement can grow into plants through the splits in the pavement.

In addition to enlarging the splits, the plants growing in the splits can also cause litter problems because they are capable of trapping litter, such as, paper wrappers as they are being blown about by the wind. This problem is especially troublesome on aircraft runways, tax-ways and aprons. Such plant growth may obscure the view of airport runway lights endangering the lives of airplane passengers. Moreover, the litter which accumulates in the runways due to the growth of plants in pavement splits can even be sucked into jet engine or into reciprocating engine intakes, to cause damage or malfunction of engines.

To alleviate the plant problem, a quick temporary solution is provided by mowing. A more permanent method has been developed which requires the splits to be routed and then sealed with either asphalt or butyl sealants. In the most severe cases, repaving the runway, taxi-way or apron may be required.

Although routing and sealing is effective for removing plants that have grown in the splits at the time the pavement is either routed and sealed or repaved, the method is not a solution for the long-term control of the plant problem in splits. That is, if the splits have been routed and sealed, the seal will eventually deteriorate thereby reopening the splits. Once the splits are reopened, the growth of plants in the reopened splits presents the same problems as those discussed above. Therefore, routing and sealing the splits does not alleviate the problem of plant growth in splits (including cracks, joints or seams). It continues to be a recurring problem.

It is known in the art that plant seedlings may be controlled by the use of pre-emergence herbicides. For example, Soper, U.S. Pat. No. 3,257,190, Soper, U.S. Pat. No. 3,111,403, Lignowski and Scott, *Trifluralin and Root Growth*, 12 Plant & Cell Physiology 701 (1971), and Eshel and Katan, *Effect of Dinitroanilines on Solanaceous Vegetables and Soil Fungi*, 20 Weed Science 243 (1972), all teach the use of 2,6-dinitroaniline as a herbicide which eliminates germinating seedlings. Furthermore, Koestler, U.S. Pat. No. 4,360,376 teaches incorporating 2,6-dinitroaniline into a microcapsule capable of releasing it. Although these references teach the use of pre-emergence herbicides to control the growth of plants, they do not provide a practical solution which may be used in long-term control of plant growth in pavement splits, including joints, cracks or seams.

By applying a herbicide in a single application to a split (a crack, joint or seam) in the pavement, the initial concentration of herbicide is much greater than needed. However, the concentration becomes too low to be a truly effective retardant with the passage of time. The concentration of herbicide in the applied area is lowered because of physical, chemical and even biological activity.

Therefore, it is desirable to provide a method and device in which the herbicide can be metered out in the split at a preselected rate. Additionally, it is desirable to provide a method and device which protects the herbicide from degradation and physical loss from the split.

Another problem with using pre-emergence herbicides, such as 2,6-dinitroaniline is that such herbicides do not eliminate existing plants. In other words, the growth of perennial plants from existing roots is largely unaffected by presence of a pre-emergence herbicide in the split.

A problem with prior art controlled release devices such as those disclosed in U.S. Pat. No. 3,864,114 (Green) is that the operation of the device disclosed in that patent is based on leaching the herbicide. Water penetrates the device and leaches out the herbicide. Generally, water degrades the herbicide in a relatively short period of time of about 2 to 6 weeks.

In light of the problem encountered by the growth of plants in pavement cracks, joints, and seams, there presently exists a need for a method and/or device which prevents such growth for extended periods of time. Such an arrangement would help minimize the amount of destruction and danger caused by plant growth in highways, airport runways, sidewalks and generally in any type of use of concrete and asphalt.

Thus, one object of the present invention is to provide a product and a method for controlling, for a prolonged period of time (2 to 10 years) the growth of plants in splits by preventing seeds from germinating and also by preventing the growth of plants from existing roots.

Another object of the present invention is to provide a controlled-release device and a method in which the release of the herbicide is driven by temperature.

A further object of the present invention is to provide a controlled release device and method in which the release rate of the herbicide and its effectiveness can be predetermined.

A still another object of the present invention is to provide a controlled release device and method in which the herbicide is protected from chemical and biological degradation prior to being released from the device.

A yet further object of the present invention is to provide environmentally superior controlled release herbicide device and method in which the herbicide is localized and does not spread far into the soil surrounding the system.

A still further object of the present invention is to provide herbicidal device which can be easily inserted into the splits and which is retained in the splits for a prolonged period of time.

Other objects of the present invention will become apparent to those skilled in the art upon studying this disclosure.

SUMMARY OF THE INVENTION

Briefly, the present invention provides a method and a device for controlling or preventing plant growth for a prolonged period of time of 2 to 10 years. The method and the device prevent seeds from germinating for extended periods of time in splits found in pavement and also prevent the growth of plants through the splits from roots of plants in the soil near the splits. A pre-emergence herbicide is incorporated into a matrix for controlled release. The polymer in the controlled release device must be capable of incorporating a herbicide. After the herbicide is incorporated into the polymer, the matrix is molded into shaped objects, such as, a band, a cord, or capsules which can then be placed into splits found in the pavement. The shaped objects are inserted into a split and are capable of maintaining a minimal effective level of herbicide for a predetermined time period. The shaped object or objects are then preferably encased by a sealer which protects them from deterioration and physically maintains them in the split.

In areas where plant roots may already exist in the soil or where root of trees or other valuable plants are not in the vicinity of the split, the present invention provides a combination of two types of shaped controlled release objects containing herbicides: one containing a pre-emergence herbicide to prevent seeds from germinating and a second containing a systemic herbicide to prevent the growth of plants from roots already in the soil. The objects are preferably sealed by a resilient polymeric sealer, such as, butyl rubber.

In accordance with a preferred embodiment of this invention, the pre-emergence herbicide can consist of a 2,6-dinitroaniline such as trifluralin. The systemic herbicide can be any approved systemic herbicide that is compatible with polymers and has an acceptable release rate, such as tebuthiuron marketed under the trade name Spike by Dow-Elanco or glyphosate marketed under the trademark Roundup by Monsanto Company. The polymer can be selected from a group consisting of thermoplastic polymers, thermoset polymers, elastomeric polymers and copolymers thereof. Once the herbicide, such as, the trifluralin is incorporated into a polymer of the controlled release device, it is extruded to form a shaped object, preferably a band, which can be conveniently placed into the splits. The band is then sealed in place by a sealer, which permits the herbicide to easily migrate there through, and is preferably resilient. The sealer is preferably either silicone or urethane or butyl rubber.

By placing a slow release device, such as, a band capable of slowly releasing a pre-emergence herbicide into the pavement cracks, joints or seams, an advantage is realized over the prior art in that seeds which are inevitably collected in such areas are prevented from successfully germinating. More importantly, the herbicide is released at such slow rates that the protection can last for long periods of time, generally 2 to 10 years, and as much as 20 years. In addition, the use of devices containing a systemic herbicide prevents the growth of plants from roots already in the soil in the vicinity of the split.

The present invention, together with attendant objects and advantages, will be best understood with reference to the detailed description below read in conjunction with the accompanying drawing.

DETAILED DESCRIPTION OF THE PREFERRED EMBODIMENTS

Figure 1:
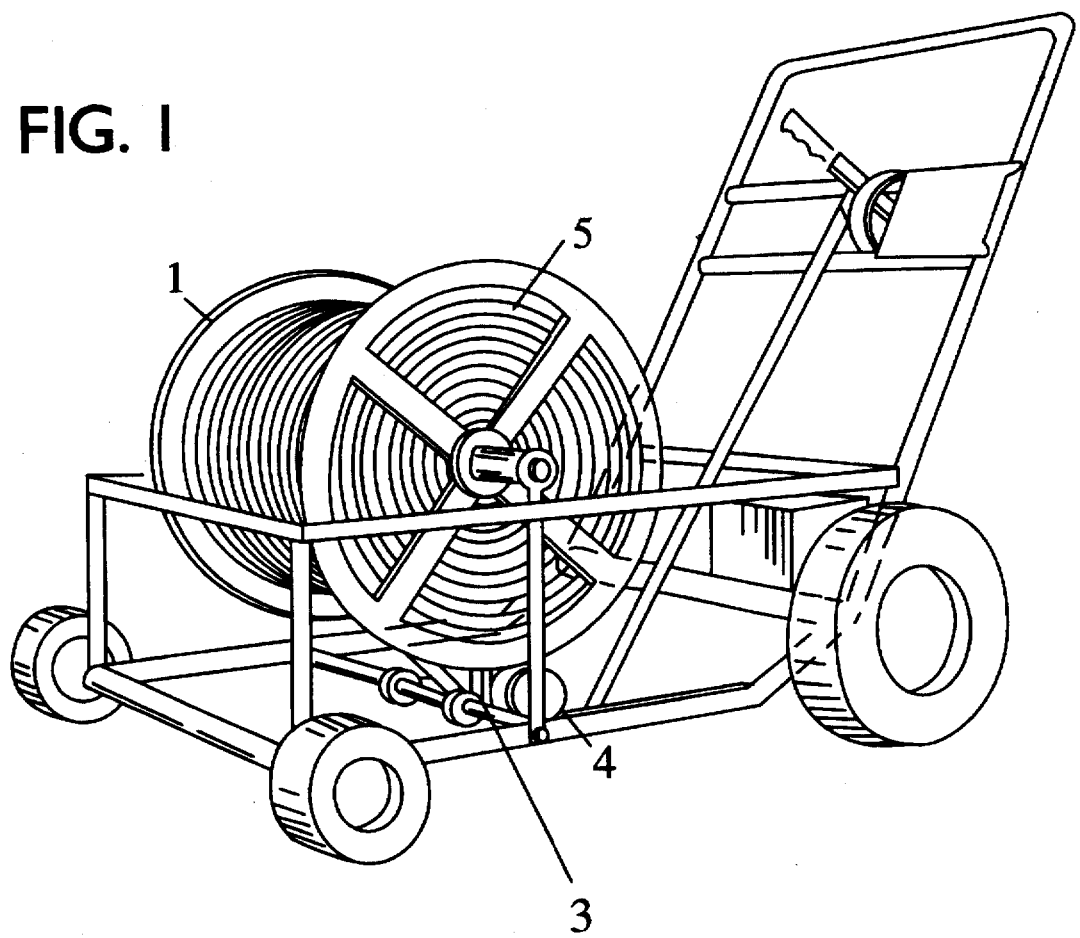
FIG. 1 is a perspective view of a preferred device which may be used in implementing the method of the present invention.

The plant control mechanism of the present invention comprises using a first polymeric matrix incorporating a pre-emergence herbicide and a second polymeric matrix incorporating a systemic herbicide. The present invention provides a method of preventing germinating seeds in splits of a pavement structure, which are either artificially or naturally created. The seeds are prevented from germinating for a prolonged period of time, generally 2 to 10 years and as much as 20 years. The prolonged protection against plant growth is effected by placing controlled release devices containing a pre-emergence herbicide in form of a shaped object, such as, a band in the splits and sealing the shaped objects with a sealer which permits the herbicide to easily travel therethrough.

The present invention also provides a method for preventing the growth of plants from roots existing in the soil near the structure. This is done by incorporating a systemic herbicide in a polymeric matrix which can be made into a shaped object. The systemic herbicide is preferably released over a period of at least about 2 years. The object or objects are then placed in the split and sealed with a sealer which permits the systemic herbicide to easily travel therethrough. Since a long term solution to plant growth is desired, the present invention incorporates the herbicide or herbicides which are used to control the plant growth into a polymeric matrices to form controlled release devices. The term "controlled release device" refers here to a device which produces controlled and sustained release of a herbicide from its matrix to its surface. The device provides a method for the controlled release of the herbicide into the surrounding environment. The herbicide released into the environment (generally soil) surrounding the system establishes an effective zone of action. Thus, the polymeric delivery system of the present invention maintains an effective dose of the active herbicide for a substantial length of time in a zone surrounding the device. If both a pre-emergence herbicide and a systemic herbicide are used in a system, two overlapping zones are formed, the systemic herbicide zone is generally larger because the pre-emergence herbicide generally travels only about a centimeter into the soil whereas systemic herbicides of this invention are slightly more water soluble and therefore are carried by water a little farther into the soil.

The controlled release systems of the present invention provide advantages over single application methods which typically result in higher than necessary concentrations immediately after treatment which subsequently within a relatively short period of time degrade to a level below the minimum effective doses. Moreover, the preferred device of the present invention releases herbicides at a high rate initially and a lower, steady rate thereafter. The high initial release rate is preferably effected by applying a sealer at an elevated temperature, preferably in a molten state. This release profile assures that the split becomes protected in a relatively short period of time and that, subsequent to reaching the minimum effective level only the amount of herbicide necessary to replace the degraded herbicide is released. This release profile diminishes potential environmental and health problems of the treatment and reduces the cost of the treatment.

Thus, by using a controlled release device, the concentration of the pre-emergence herbicide can be maintained at a concentration above the "minimal effective level" necessary to stop germinating plants. Similarly, the systemic herbicide is released from the controlled release device at a rate that maintains its concentration in the above its minimal effective level. As used in this specification and the appended claims, the term "minimal effective level" is defined with respect to pre-emergence herbicides to mean the level of herbicide necessary to prevent seeds from germinating. The term "minimal effective level" is defined with respect to systemic herbicide as the level of systemic herbicide that is necessary to prevent plants from growing.

It has been found that polymers serve as effective release devices because they can act as both reservoirs and release-regulating mechanisms for the herbicide. Moreover, they can protect the herbicide from degradation. A more detailed description of "controlled release devices" is given in U.S. patent application Ser. Nos. 06/555,113, filed Nov. 23, 1983, which is a continuation in part of 06/314,809, and 06/314,810 both filed on Oct. 26, 1981; 07/086,757, filed Aug. 18, 1987, 07/072,080 filed Jul. 10, 1987; and 07/091,918 filed Sep. 1, 1987. The contents of these applications being incorporated herein by reference.

Preferably, a pre-emergence herbicide is selected on the basis of being capable of effectively retarding or preventing germination of seeds. In pavement applications, 2,6-dinitroanilines have been found to be suitable retardants. By way of example, some suitable 2,6-dinitroanilines are trifluralin commercially available as Treflan, benfluralin available as Benfin, insopropalin available as Pearlan, oryzalin available as Surflan, ethalfluralin available as Sonalan, pandimethalin available as Prowke and profluralin available as Tolban. Preferably, the 2,6-dinitroanilines are trifluralin and benefin. The most preferred 2,6-dinitroaniline is trifluralin. The preferred concentration of pre-emergence herbicides in the polymer matrix range from about 10 to about 25 of the total weight of the matrix, especially preferred is the range from about 15 to about 20 percent.

Any systemic general purpose (non-selective) herbicide can be used in connection with the present invention. The selection of a specific herbicide depends on the application. Examples of preferred systemic herbicides suitable for use in the present invention include tebuthiuron marketed by Dow Elanco under the trade name Spike and glyphosate marketed by Monsanto Company under the tradename Roundup. Tordon and diuron are examples of other systemic herbicides that can be employed.

Polymer selection for the controlled release device depends upon the extreme conditions found in concrete or asphalt. Temperatures can vary from below freezing to nearly 50° C. Additionally, the pavement encounters various types of moisture such as water and ice. Finally, the selection of the polymer must account for the characteristics of the herbicides and provide the desired release rates.

Preferred polymers capable of withstanding such adverse conditions and providing the desired release rates for the pre-emergence herbicide, such as, 2,6-dinitroaniline, include isoprene, low density (LD) polyethylene and high density (HD) polyethylene. However, it is possible to use other polymers selected from the group consisting of thermoset polymers, thermoplastic polymers, elastomeric polymers and copolymers thereof. By way of example, some other possible polymers include vinyl acetate, urethane, polyester, silicone and neoprene. The preferred polymers for systemic herbicides are silicones and urethanes. Silicones and urethanes are preferred primarily because their matrices provide a relatively faster release rate for polar compounds. It has been discovered that it is advantageous to release the systemic herbicide quicker than the pre-emergence herbicide. It will be recognized by those skilled in the art that other suitable polymers may also be used with the present invention depending on the particular use contemplated. The preferred concentration of systemic herbicides in the polymer matrix range from about 5 percent to about 10 percent of the total weight of the matrix, especially preferred is range from about 8 to about 10 percent.

In addition, it is advantageous to add a filler and/or carrier to the controlled release device to optimize the loading of the polymer. The inclusion of such a substance allows greater amounts of herbicide to be loaded into the desired polymer while at the same time assisting in the release rate of herbicide. Carbon black is the preferred carrier. The preferred amount of carbon black is from about 2 to about 10 percent by weight of the total weight of the device.

To form the controlled release device of the present invention, a pre-emergence herbicide, such as 2,6-dinitroaniline and a systemic herbicide, such as tebuthiuron, is incorporated into the polymer by mixing. The mixing should be sufficient to allow an even distribution of herbicide throughout the polymer. A more detailed description of the mixing is given in U.S. patent application Ser. No. 06/555,113 filed on Nov. 23, 1983 which is a continuation-in-part of U.S. patent applications, 06/314,809 and 06/314,810 both filed on Oct. 26, 1981. Methods for obtaining the release rates are described in patent application 07/303,770 filed on Jan. 30, 1989.

Figure 2:
FIG. 2 is a perspective view of a preferred embodiment of this invention.
Figure 3:
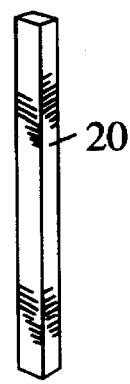
FIG. 3 is a perspective view of another preferred embodiment of this invention.

Once loaded, the polymer matrices are then molded into shape objects, such as, bands and allowed to cool so as they would maintain the desired shapes. As shown in FIGS. 2 and 3, the bands can be molded, for example, into a cord 10 or a flat strip 20. Preferably, the molding is accomplished by means of extrusion which is known in the art. The band can be designed with varying diameters and with differing amount of herbicide.

However, to prevent seeds from germinating for extended periods of time, an amount of the pre-emergence herbicide sufficient to establish and maintain a minimal effective level in a zone surrounding the device must be loaded into a polymer matrix. Similarly, to prevent the growth of plants from roots already existing in the soil, a sufficient amount of the systemic herbicide must be incorporated into the polymer matrix containing the pre-emergence herbicide or into a separate polymeric matrix to establish and maintain a minimal effective level of herbicide in the soil surrounding the device. It has been discovered that for the minimal effective level of 2,6-dinitroaniline is about 10 parts per million of soil. Similarly, it has been discovered that the minimal effective level of the systemic herbicide, such as, tebuthiuron is about 2 ppm of soil.

Table 1 provides longevity estimates of "minimum effective levels" for the three preferred polymer cord systems at two loading concentrations, 15 and 30%, and at four different cord diameters. The estimated release rates were calculated at a temperature of 45° C. because of the high temperatures found on pavements. Table 1 is provided by way of explanation and illustration. As such, the table is not to be viewed as limiting the scope of the invention.

TABLE 1

| Polymer/ Cylinder dia (in) | Est Rel Rate (45° C.) (µg/cm2/day) | Est Longevity (15%) (yr) | Est Longevity (30%) (yr) |
| --- | --- | --- | --- |
| Isoprene |  |  |  |
| 0.25 | 250 | 2.67 | 5.35 |
| 0.312 | 250 | 3.43 | 6.87 |
| 0.375 | 250 | 4.21 | 8.42 |
| 0.5 | 250 | 5.76 | 11.52 |
| LD PE |  |  |  |
| 0.25 | 200 | 3.34 | 6.68 |
| 0.312 | 200 | 4.29 | 8.59 |
| 0.375 | 200 | 5.26 | 10.53 |
| 0.5 | 200 | 7.20 | 14.40 |
| HD PE |  |  |  |
| 0.25 | 120 | 5.57 | 11.14 |
| 0.312 | 120 | 7.15 | 14.31 |
| 0.375 | 120 | 8.77 | 17.54 |
| 0.5 | 120 | 12.00 | 24.01 |

As can be seen from the table, the release rates of the herbicide can vary with the selection of the polymer matrix. However, a "minimal effective level" can be maintained for at least 3 to 5 years. Preferably, the concentration in parts by weight of the herbicide should range from about 10 to about 30, the concentration of polymer from about 50 to about 90 and the concentration of filler from about 10 to about 30.

Preferably, the crack which is to be processed is first routed to remove existing undesired plants. After the crack has been routed, the band described above is placed in the crack. The band which is preferably the size of the crack is generally embedded at a depth of about 1 to 2 inches. Once in place, a backer rod typically made of polyethylene can be put on top of the band. After the band is applied to the crack, the crack containing a band therein is sealed using a sealing material, such as hot butyl rubber, asphalt or even concrete. It should be noted that the mentioned sealants were used by way of example and do not limit the scope of this invention.

Preferably, the sealant is applied immediately upon the insertion of the band because of the possible detrimental effects to the band caused by sunlight and the weather. However, a leeway of a few hours is permitted. Upon sealing the band, the heat given off by the molten sealant advantageously causes the band to give off an immediate burst of herbicide which eventually tapers to the desired steady state.

FIG. 1 illustrates a preferred apparatus which may be used to implement the method of the present invention. The band, in the form of a cord 5, is transported to the work area where it will be placed in a crack on a cart generally shown at 6. The cart 6 comprises a reel 1 upon which the cord 5 is wound. Below the reel 1 is a stationary clevis 3 through which cord 5 travels. A wheel 4 also disposed beneath the reel 1 can be adjusted lower or raise the reel 1. The cart 6 preferably also includes a heating mechanism to heat the cord 5 to allow for easier application of the band 5 in pavement cracks. The heating mechanism 2 may comprise, for example, a 12 volt battery and an electrical resistance heating element. This heating mechanism is particularly useful since the rolled cord 5 will tend to retain its rolled shape, commonly referred to as a "memory effect." The heating of the rolled cord 5 by means of the heating mechanism will tend to eliminate this memory effect. Additionally, the heating makes the band or cord more flexible and thus easier to apply.

After being transported, the band 5 is placed into the split in the pavement. However, before placement, the split must be routed. With the band in place, the split is resealed. The split can be resealed by a variety of sealants. Resilient polymers which permit easy travel of herbicides therethrough are the preferred sealers. Currently, the most preferred sealer is butyl rubber. However, asphalt is the most common sealing material.

In conclusion, advantages are realized by placing a band capable of slowly releasing herbicide into pavement splits. One advantage is that the plants that collect in the splits are prevented from germinating. More importantly, the invention provides a long-term solution for the plant growth problem and thereby, eliminates the need for frequent repair and reseal of pavement structures such as runways and sidewalks.

Figure 4:
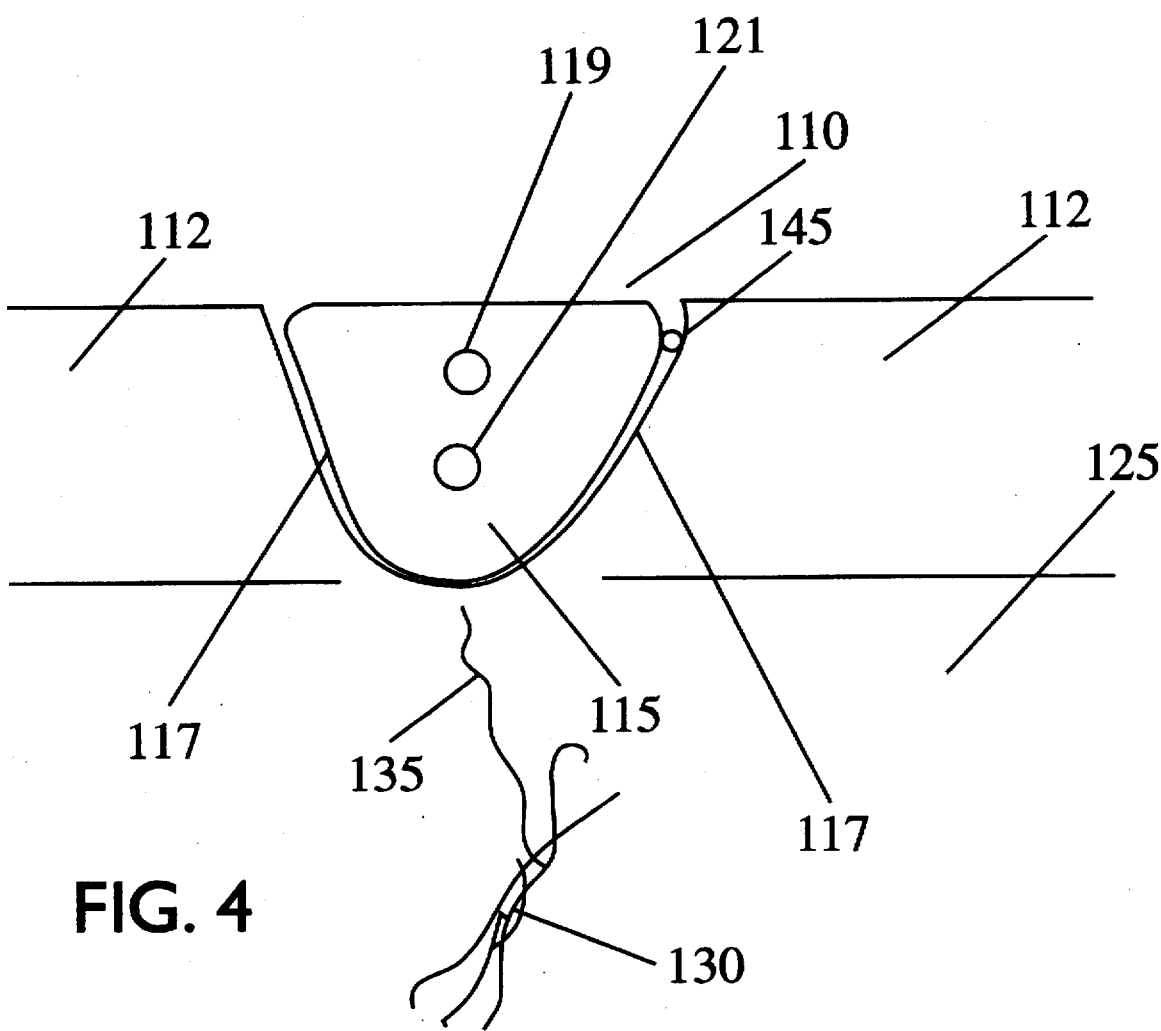
FIG. 4 is a cross-sectional view of yet another preferred embodiment of the present invention.

Referring now to FIG. 4, there is shown there a cross-section of a crack generally designed by a numeral 100 in a pavement structure 112 filled in accordance with the present invention by a system constructed in accordance with the present invention. The crack 10 is sealed by a sealer 15 composed of butyl rubber. The sealer fits tightly against the walls 117 of the crack 110. Inside the sealer 115 there is a controlled release device 119 in shape of a continuous cord. The controlled release device 119 contains a pre-emergence herbicide, such as, trifluralin. Also inside the sealer 115, there is a controlled release device 121 which contains a systemic herbicide, such as Roundup® or Spike®.

The matrix of device 119 is preferably made of a high density polyethylene and carbon black. The preferred composition of this device is high density polyethylene—70 parts, carbon black 5 parts and Treflan 25 parts. The matrix of device 121 is preferably made of silicone or urethane. The preferred composition of this device is silicone or urethane—90 parts and Spike—10 parts. The preferred silicone is silicone 3112.

In operation, the crack 10 is first routed to remove dirt and plants therefrom. Then, the cord 119 and the cord 121 are placed in the crack 110. The crack 110 is then filled with a molten butyl rubber seal 115. The seal 115 encases the cords 119 and 121 and physically maintains them in position in the crack 110. The butyl rubber protects the herbicides in the cords 119 and 121 from degradation.

The heat from the sealer 115 causes a release of a significant dose of the herbicides from the polymeric matrices of cords 119 and 121. The herbicides traverse the butyl rubber and migrate to the interface between the wall 117 of the pavement 112 and the outside surface of the butyl rubber seal 115. It has been discovered that for trifluralin, the minimal effective concentration at the interface is about 10 ppm of soil. The pre-emergence herbicide generally travels only less than about one centimeter from the interface between the seal 115 and the wall 117 into the soil 125. The systemic herbicide, however, travels further into the soil 115 and establishes a herbicidal zone in the soil in which plants are prevented from growing. When a root, such as root 130 existing in the soil grows a shoot, such as, shoot 135, which enters the herbicidal zone, the systemic herbicide is absorbed by the shoot and/or root 135. The shoot 135 and root 130 are destroyed.

Similarly, pre-emergence herbicide forms a zone around the seal 115. If a seed, such as, seed 145 finds its way into a space between the seal 115 and the wall 117, the pre-emergence herbicide prevents such seed from germinating.

It should be apparent that a wide range of changes and modifications can be made to the preferred embodiments described above. It is therefore intended that the foregoing description be regarded as illustrative rather than limiting, and that it be understood that it is the following claims, including all equivalents, which are intended to define this invention.

We claim:

1. A method for protecting, for a prolonged period of time, the structural integrity of pavement with a split therein, said method comprising the following steps;

(a) placing a polymeric matrix containing a pre-emergence herbicide in said split;

(b) sealing said split with a sealer permitting migration of the herbicide thereinto and therethrough;

(c) allowing the temperature of the sealer to cause said herbicide to release from said polymeric matrix and migrate into and through said sealer onto the interface between the sealer and the split and into the soil surrounding the split to form a herbicidal zone adjacent said sealer, the concentration of the pre-emergence herbicide in said zone being sufficiently high to prevent germination of seeds therein;

(d) allowing the temperature of the sealer to continually release said pre-emergence herbicide from said polymeric matrix and migrate into and through said sealer into said herbicidal zone to maintain the herbicide in said zone at a sufficiently high concentration to prevent germination of seeds therein.

2. The method of claim 1 wherein the sealer being used for sealing is applied in step (b) in a molten state causing a rapid release of said herbicide in step (c).

3. The method of claim 1 wherein the pre-emergence herbicide is 2,6 dinitroaniline.

4. The method of claim 1 wherein the pre-emergence herbicide is a trifluralin.

5. The method of claim 3 wherein the polymeric matrix comprises a mixture of low density polyethylene and high density polyethylene.

6. The method of claim 3 wherein the ratio of low density polyethylene to high density polyethylene is about 4 to 1 by weight.

7. The method of claim 1 wherein the concentration of the pre-emergence herbicide is sufficient to produce and maintain a minimal effective level of the herbicide around the sealer.

8. The method of claim 3 wherein the concentration of 2,6 dinitroaniline is in the range from about 10 to about 25 percent of the total weight of the polymeric matrix.

9. The method of claim 4 wherein the concentration of trifluralin near the surface of the sealer is at least about 10 ppm.

10. The method of claim 4 wherein the polymeric matrix further comprises carbon black.

11. The method of claim 10 wherein the concentration of carbon black is in the range from about 2 to about 10 percent of the weight of the polymeric matrix.

12. A protective system for protecting, for a prolonged period of time the structural integrity of pavement that includes at least one split, said system comprising:

(a) a first polymeric matrix;

(b) a pre-emergence herbicide dispersed throughout said first polymeric matrix;

(c) a sealer having voids therein surrounding said first polymeric matrix, the voids of said sealer being sufficiently large to allow herbicides to traverse said sealer at a rate at least as high as the rate at which said herbicide is released from said polymeric matrix.

* * * * *